(12) United States Patent
Dyke et al.

(10) Patent No.: US 6,403,791 B1
(45) Date of Patent: Jun. 11, 2002

(54) HETEROCYCLIC COMPOUNDS AND THEIR THERAPEUTIC USE

(75) Inventors: Hazel Joan Dyke; Alan Findlay Haughan; Christopher Lowe; George Martin Buckley; Richard John Davenport; Andrew Sharpe; Hannah Jayne Kendall; Verity Margaret Sabin; John Gary Montana, all of Cambridge; Catherine Louise Picken, Cheshire, all of (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/779,963

(22) Filed: Feb. 9, 2001

(30) Foreign Application Priority Data

Feb. 11, 2000 (GB) .............................................. 0003256

(51) Int. Cl.⁷ .................. C07D 413/04; A61K 31/5377
(52) U.S. Cl. ....................... 544/140; 544/109; 544/114; 544/139; 548/236; 548/247; 514/396; 514/397; 514/407; 514/373.1; 514/233.8
(58) Field of Search ................................. 514/375, 379, 514/396, 397, 406, 407, 372.5, 373.1; 544/109, 114, 137, 140; 548/236, 247

(56) References Cited

U.S. PATENT DOCUMENTS 5,804,588 A 9/1998 Dyke et al.

FOREIGN PATENT DOCUMENTS

| JP | 06107646 | * | 4/1994 |
| WO | 9822460 | | 5/1999 |
| WO | 9964423 | | 12/1999 |

* cited by examiner

Primary Examiner—Floyd D. Higel
Assistant Examiner—Kamal Saeed
(74) Attorney, Agent, or Firm—Saliwanchik, Lloyd & Saliwanchik

(57) ABSTRACT

A compound of the formula

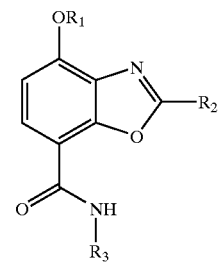

(i)

wherein
$R_1$ is $C_{1-3}$ alkyl optionally substituted with one or more fluorines;
$R_2$ is $C_{1-6}$ alkyl, cycloalkyl or $NR_4R_5$;
$R_3$ is a pyrazole, imidazole or isoxazole group of partial formula (A), (B) or (C)

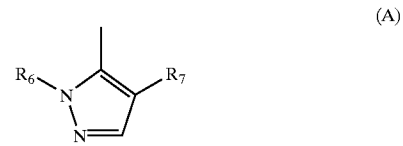

(A)

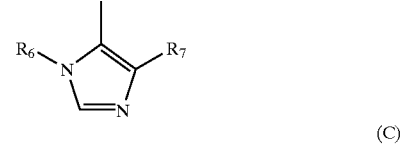

(B)

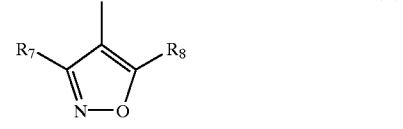

(C)

$NR_4R_5$ is a nitrogen-containing heterocyclic ring;
$R_6$ is $C_{1-3}$ alkyl; and
$R_7$ and $R_8$, which are the same or different, each represents $C_{1-3}$ alkyl, halogen, $CF_3$ or CN;
or a pharmaceutically-acceptable salt thereof.

15 Claims, No Drawings

HETEROCYCLIC COMPOUNDS AND THEIR THERAPEUTIC USE

FIELD OF THE INVENTION

The present invention relates to novel heterocyclic compounds and to their formulation and use as pharmaceuticals.

BACKGROUND OF THE INVENTION

The modes of action of phosphodiesterases and also tumour necrosis factors (TNF), and the therapeutic utilities of inhibitors thereof, are described in WO-A-97/44036 and U.S. Pat. No. 5,804,588, the contents of which are incorporated herein by reference. WO-A-98/22460 and U.S. patent application Ser. No. 09/422,473, filed Nov. 17, 1997, disclose benzoxazoles that also have such activity.

SUMMARY OF THE INVENTION

This invention provides novel compounds having therapeutic utility, in particular for the treatment of disease states associated with proteins which mediate cellular activity, for example by inhibiting TNF and/or PDE IV. According to the invention, the compounds are of formula (i):

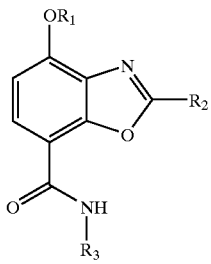

wherein
$R_1$ is $C_{1-3}$ alkyl optionally substituted with one or more fluorines;
$R_2$ is $C_{1-6}$ alkyl, cycloalkyl or $NR_4R_5$;
$R_3$ is a pyrazole, imidazole or isoxazole group of partial formula (A), (B) or (C)

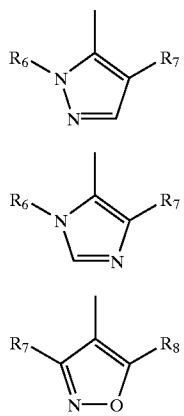

$NR_4R_5$ is a nitrogen-containing heterocyclic ring, such as morpholine, pyrrolidine, piperidine or azetidine;
$R_6$ is $C_{1-3}$ alkyl, and
$R_7$ and $R_8$, which are the same or different, each represents $C_{1-3}$ alkyl, halogen, $CF_3$ or CN;
or a pharmaceutically-acceptable salt thereof.

In summary, the compounds of the invention represent a selection within the scope of WO-A-98/22460. The novel compounds have superior pK, and therefore enhanced bioavailability.

This invention provides also a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

DESCRIPTION OF THE INVENTION

The term "$C_{1-6}$ alkyl" means a straight or branched chain alkyl moiety having one to six carbon atoms, including, for example, methyl, ethyl, propyl, isopropyl, n-butyl, isobutyl, sec-butyl, tert-butyl, pentyl, hexyl and the like. The term "$C_{1-3}$ alkyl" means methyl, ethyl, propyl or isopropyl.

One group of compounds of the invention is of formula (i) in which $R_1$ is $CH_3$ or $CHF_2$.

Another group of compounds of the invention is of formula (i) in which $R_2$ is ethyl, cyclopropyl or $NR_4R_5$.

In one particular group of compounds of the invention $R_3$ is a pyrazole group in which $R_6$ is in particular $CH_3$ or $C_2H_5$ and $R_7$ is especially CN, Cl, $CH_3$, $C_2H_5$, Br or $CF_3$. Especially preferred is where $R_6$ is in particular $CH_3$ and $R_7$ is especially CN, $CH_3$, or $CF_3$.

$R_3$ in another group of compounds of formula (i) is an imidazole group in which $R_6$ is in particular $CH_3$ or $C_2H_5$ and $R_7$ is particularly CN or $CH_3$.

A further group of compounds of the invention is where $R_3$ is an isoxazole group in which $R_7$ is in particular $CH_3$, $CF_3$, $C_2H_5$ or CN and $R_8$ is especially $CH_3$, $CF_3$, $C_2H_5$ or CN. Especially preferred is where $R_7$ is in particular $CH_3$, $CF_3$, or CN and $R_8$, is especially $CH_3$, $CF_3$, or CN.

Certain of the compounds of formula (i) which contain a basic group form acid addition salts. Suitable acid addition salts include pharmaceutically-acceptable inorganic salts such as the sulphate, nitrate, phosphate, borate, hydrochloride and hydrobromide, and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

Compounds of the invention may be prepared from suitable carboxylic acids (ii) and amines (iii), as described in WO-A-98/22460

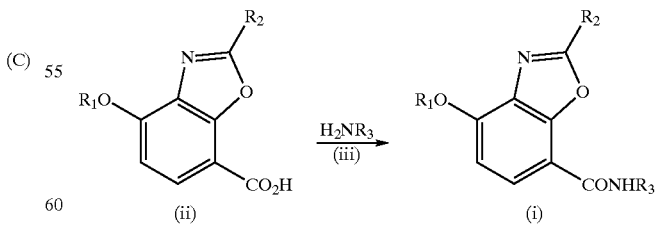

Carboxylic acids of formula (ii) are prepared using standard conditions known to those skilled in the art such as carboxylation of bromides of formula (iv) or (vi) using carbon monoxide gas and an organopalladium catalyst. Amines of formula (iii) are either commercially available, previously described compounds, or are prepared using standard conditions known to those skilled in the art.

Bromides of formula (vi) are either previously described or prepared using standard conditions known to those skilled in the art. For example, compounds of formula (vi) in which $R_1$ represents methyl and $R_2$ represents $NR_4R_5$ are conveniently prepared from 4-methoxy-2-sulfanylmethylbenzooxazole by displacement of the 2-methylsulfanyl group on heating with the appropriate amine $HNR_4R_5$.

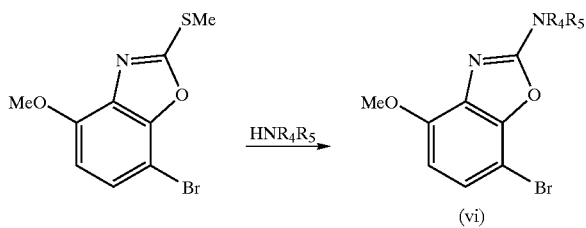

Compounds in which $R_1$ represents difluoromethyl by be prepared from intermediates in which $R_1$ represents methyl by demethylation followed by difluoromethylation. Demethylation of compounds of formula (vi) may be carried out under standard conditions known to those skilled in the art, for example by using ethane thiol and sodium hydride in dimethylformamide at elevated temperature, or with boron tribromide in dichloromethane. Difluoromethylation of the phenols (v) may be achieved using any suitable conditions known to those skilled in the art, for example by passing chlorodifluoromethane gas through a solution of the appropriate phenol in a mixture of aqueous sodium hydroxide and dioxane at elevated temperature to give compounds of formula (iv)

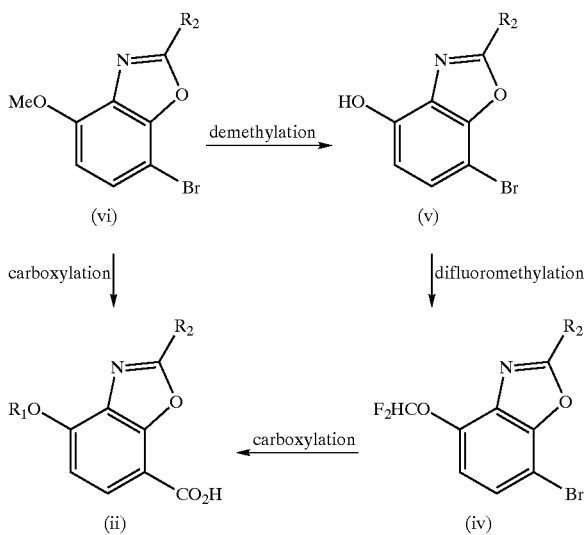

The invention includes the prevention and treatment of TNF-mediated disease or disease states, by which is meant any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biological responses and binds to the same cellular receptor, both TNF-α and TNF-β are inhibited by compounds of the present invention and thus are herein referred to collectively as "TNF" unless specifically delineated otherwise.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically-acceptable form. By pharmaceutically-acceptable form is meant, inter alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%. When used herein the term "pharmaceutically-acceptable" encompasses materials suitable for both human and veterinary use.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions, the compound can be dissolved in water for injection and filter-sterilised before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

Assay Methods

The assays used to confirm the phosphodiesterase IV inhibitory activity of compounds of formula (I) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI1640+1% foetal calf serum in the presence and absence of inhibitors. LPS (Lipopolysaccharide (endotoxin); 100 ng/ml) is added and cultures are incubated for 22 h at 37° C. in an atmosphere of 95% air/5% $CO_2$. Supernatants are tested for TNFα by ELISA (Enzyme linked immunosorbent assay) using commercially available kits.

Activity in a guinea pig lung model is measured using the procedures described by Mauser et al, Am. Rev. Respir. Dis. 148:1623 (1993), and Am. J. Respir. Crit. Care Med. 152:467 (1995).

The compound of Example 7 of WO-A-98/22460 (see the assay described there) achieves $C_{max}$ 15 ng/ml when dosed orally at 5 mg/kg to guinea pigs. Example 1 herein (representative of the present invention) achieves $C_{max}$= 4370 ng/ml when dosed orally at 3 mg/kg to guinea pigs.

The following Examples illustrate the invention.

INTERMEDIATE 1

4-Methoxy-2-methylsulfanylbenzooxazole n-Butyllithium (20.13 ml of a 1.6N solution in hexanes) was added gradually to a solution of 4-methoxybenzoxazole (4.0 g) in tetrahydrofuran (150 ml) cooled in a cardice-acetone bath under an atmosphere of nitrogen. After stirring for 20 minutes dimethyl disulfide (2.9 ml) was added. The mixture was warmed to room temperaturee and stirred for 18 hours. The tetrahydrofuran was removed by evaporation in vacuo and the residue partitioned between ethyl acetate (150 ml) and water (150 ml). The organics were washed with water (150 ml), dried over magnesium sulphate, filtered and the solvent removed in vacuo. Purification by column chromatography on silica eluting with 10% ethyl acetate in heptane afforded the title compound as a white solid (2.63 g).

TLC $R_f$ 0.48 (20% ethyl acetate in heptane).

INTERMEDIATE 2

7-Bromo-4-methoxy-2-methylsulfanylbenzooxazole

N-Bromosuccinimide (2.4 g) was added to a solution of 4-methoxy-2-methylsulfanylbenzooxazole (2.63 g) in acetonitrile (80 ml) and the mixture stirred for 18 hours. It was then partitioned between dichloromethane (200 ml) and water (200 ml). The organics were washed with water (200 ml), dried over magnesium sulphate, filtered and the solvent removed in vacuo. Purification by column chromatography on silica eluting with 10% ethyl acetate in heptane afforded the title compound as a white solid (1.25 g).

TLC $R_f$ 0.32 (20% ethyl acetate in heptane).

INTERMEDIATE 3

7-Bromo-4-methoxy-2-(morpholin-4-yl)-benzooxazole

A mixture of 7-bromo-4-methoxy-2-methylsulfanylbenzooxazole (10.0 g) and morpholine (6.6 ml) were heated at 80° C. for 18 hours. Purification by chromatography on silica eluting with 20–100% ethyl acetate in heptane afforded the title compound as an off-white solid (11.6 g).

TLC $R_f$ 0.44 (50% ethyl acetate in hexane).

The following compounds were prepared in a similar manner as above.

INTERMEDIATE 4

7-Bromo-4-methoxy-2-(piperidin-1-yl)-benzooxazole

Starting from 7-bromo-4-methoxy-2-methylsulfanylbenzooxazole (10.0 g) and piperidine (3.8 ml). Purification by chromatography on silica eluting with 30–100% ethyl acetate in hexane afforded the title compound as an off-white solid (10.7 g).

TLC $R_f$ 0.50 (50% ethyl acetate in hexane).

INTERMEDIATE 5

2-(Azetidin-1-yl)7-bromo-4-methoxybenzooxazole

Starting from 7-bromo-4-methoxy-2-methylsulfanylbenzooxazole (4.8 g) and azetidine (1.0 g). Purification by chromatography on silica eluting with 50% ethyl acetate in heptane afforded the title compound as a pink solid (2.95 g).

TLC $R_f$ 0.42 (ethyl acetate).

INTERMEDIATE 6

7-Bromo-2-ethylbenzooxazol-4-ol

To a stirred suspension of sodium hydride (1.6 g) (60% dispersion in mineral oil) in dry DMF (20 ml) under an atmosphere of nitrogen was added dropwise a solution of ethanethiol (2.9 ml) in DMF (3 ml). After stirring at room temperature for 15 mins a solution of 2-ethyl-7-methoxybenzoxazole (1.0 g) in DMF (10 ml) was added slowly. The reaction mixture was heated at 150° C. for 90 mins. The solvent was removed in vacuo and the residue dissolved in saturated ammonium chloride solution (50 ml) and extracted with ethyl acetate (100 ml). The aqueous layer was acidified to pH 4 with 1N hydrochloric acid and extracted with ethyl acetate (100 ml). The organic layers were combined, washed with brine (50 ml), separated, dried over magnesium sulphate, filtered and the solvent removed in vacuo. Purification by column chromatography on silica eluting with 20–30% ethyl acetate in hexane afforded the title compound as an off-white solid (0.62 g).

TLC $R_f$ 0.21 (20% ethyl acetate in hexane).

INTERMEDIATE 7

7-Bromo-2-(morpholin-4-yl)-benzooxazol-4-ol

A solution of boron tribromide (25.6 ml of a 1.0M in dichloromethane) was added slowly to a stirred solution of 7-bromo-4-methoxy-2-(morpholin-4-yl)-benzooxazole (4.0 g) in dry dichloromethane (100 ml) under an atmosphere of nitrogen. The reaction mixture was stirred at room temperature for 90 mins. The mixture was partitioned between sodium hydrogencarbonate solution (50 ml) and dichloromethane (100 ml). The organic layer was separated, dried over magnesium sulphate, filtered and the solvent removed in vacuo. Purification by column chromatography on silica eluting with 30–50% ethyl acetate in heptane afforded the title compound as an off-white solid (1.64 g).

TLC $R_f$ 0.28 (50% ethyl acetate in hexane).

The following compounds were prepared in a similar manner to the above.

INTERMEDIATE 8
7-Bromo-2-(piperidin-1-yl)-benzooxazol-4-ol

Starting from 7-bromo-4-methoxy-2-(piperidin-1-yl)-benzooxazole (9.0 g). Trituration in diethyl ether afforded the title compound as a pale brown solid (7.46 g).

TLC $R_f$ 0.35 (50% ethyl acetate in hexane).

INTERMEDIATE 9
2-(zetidin-1-yl)-7-bromobenzooxazol-4-ol

Starting from 2-(azetidin-1-yl)-7-bromo-4-methoxybenzooxazole (1.95 g). Purification by column chromatography eluting with 50% ethyl acetate in dichloromethane followed by trituration in diethyl ether/hexane afforded the title compound as a white solid (1.42 g).

TLC $R_f$ 0.17 (50% ethyl acetate in heptane).

INTERMEDIATE 10
7-Bromo-4-difluoromethoxy-2-ethylbenzooxazole

A solution of sodium hydroxide (1.0 g) in water (3 ml) was added dropwise to a stirred solution of 7-bromo-2-ethylbenzooxazol-4-ol (2.0 g) in dioxane (60 ml) heated to 100° C. Chlorodifluoromethane was bubbled through the reaction mixture for 20 mins after which the mixture was allowed to cool to room temperature. The solvent was removed in vacuo and the residue diluted with water (30 ml) and acidified to pH 3 with 1N hydrochloric acid. This was extracted with ethyl acetate (200 ml), washed with brine (30 ml), the organic layer separated, dried over magnesium sulphate, filtered and the solvent removed in vacuo. Purification by column chromatography on silica eluting with 10% ethyl acetate in hexane afforded the title compound as a colourless oil (1.9 g).

TLC $R_f$ 0.72 (20% ethyl acetate in hexane).

The following compounds were prepared in a similar manner to the above.

INTERMEDIATE 11
7-Bromo-4-difluoromethoxy-2-(morpholin-4yl)-benzooxazole

Starting from 7-bromo-2-(morpholin-4-yl)-benzooxazol-4-ol (1.7 g). Purification by column chromatography on silica eluting with 20–40% ethyl acetate in heptane afforded the title compound as a white solid (0.98 g).

TLC $R_f$ 0.38 (20% ethyl acetate in hexane).

INTERMEDIATE 12
7-Bromo-4-difluoromethoxy-2-(piperidin-1-yl)-benzooxazole

Starting from 7-bromo-2-(piperidin-1-yl)-benzooxazol-4-ol (2.0 g). Removal of the solvent in vacuo afforded the title compound as an orange oil (2.15 g).

TLC $R_f$ 0.68 (50% ethyl acetate in hexane).

INTERMEDIATE 13
2-(Azetidin-1-yl)-7-bromo-4-difluoromethoxybenzooxazole

Starting from 2-(azetidin-1-yl)-7-bromobenzooxazol-4-ol (1.46 g). Purification by column chromatography on silica eluting with 30% ethyl acetate in heptane afforded the title compound as a white solid (0.75 g).

TLC $R_f$ 0.44 (50% ethyl acetate in heptane).

INTERMEDIATE 14
4-Difluoromethoxy-2-ethylbenzooxazole-7-carboxylic acid

Palladium(II) acetate (54 mg), 1,3-bis(diphenylphosphino)propane (198 mg) and triethylamine (3.3 ml) were added to a solution of 7-bromo-4-difluoromethoxy-2-ethylbezooxazole (0.7 g) in THF/water (30 ml/15 ml). The mixture was heated at 90° C. under 100 psi of carbon monoxide for 4 days. The reaction mixture was allowed to cool to room temperature and the pressure released. The THF was removed in vacuo and the residue diluted with water (10 ml) and washed with ethyl acetate (50 ml). The aqueous layer was acidified to pH 3 with 2N hydrochloric acid and extracted with ethyl acetate (150 ml). Separation of the organic layer, drying over magnesium sulphate, filtering and removal of the solvent in vacuo afforded the title compound as an off-white solid (0.47 g).

TLC $R_f$ 0.37 (50% ethyl acetate in hexane).

The following compounds were prepared in a similar manner to the above.

INTERMEDIATE 15
4-Methoxy-2-(morpholin-4-yl)-benzooxazole-7-carboxylic acid

Starting from 7-bromo-4-methoxy-2-(morpholin-4-yl)-benzooxazole (0.98 g) to afford the title compound as a white solid (0.59 g).

TLC $R_f$ 0.20 (ethyl acetate).

INTERMEDIATE 16
4-Difluoromethoxy-2-(morpholin-4-yl)-benzooxazole-7-carboxylic acid Starting from 7-bromo-4-difluoromethoxy-2-(morpholin-4-yl)-benzooxazol (0.83 g) to afford the title compound as a white solid (0.69 g).

TLC $R_f$ 0.46 (90:10:1 dichloromethane:methanol:triethylamine).

INTERMEDIATE 17
4-Difluoromethoxy-2-(iperidin-1-yl)-benzooxazole-7-carboxylic acid Starting from 7-bromo-4-difluoromethoxy-2-(piperidin-1-yl)-benzooxazole (2.0 g). Purification by column chromatography on silica eluting with 2.5% to 10% methanol in dichloromethane afforded the title compound as a white solid (1.08 g).

TLC $R_f$ 0.47 (10% methanol in dichloromethane).

INTERMEDIATE 18
2-(Azetidin-1-yl)-4-difluoromethoxybenzooxazole-7-carboxylic acid Starting from 2-(azetidin-1-yl)-7-bromo4-difluoromethoxybenzooxazole (0. 747g) to afford the title compound as a pale pink solid (0.477 g).

TLC $R_f$ 0.38 (70% ethyl acetate in heptane).

INTERMEDIATE 19
2-Ethyl-4-methoxybenzoxazole-7-carboxylic acid

A mixture of 7-bromo-2-ethyl-4-methoxybenzoxazole (0.7 g), triphenylphosphine (0.273 g) bis(triphenylphosphine)palladium(II)chloride (0.1 25 g) and triethylamine (3.9 ml) in tetrahydrofuran (19 ml) and water (6.2 ml) were heated to 80° C. in a Parr apparatus under an atmosphere of carbon monoxide gas at 140 psi for 3 days. The mixture was then allowed to cool to ambient temperature and concentrated in vacuo. It was basified to pH14 using 1M sodium hydroxide solution and extracted with ethyl acetate (2×50 ml). The aqueous phase was acidified to pH5 using glacial acetic acid and extracted with dichloromethane. The combined dichloromethane extracts were dried (MgSO$_4$) and evaporated in vacuo to give the title compound as a beige solid (0.40 g).

TLC R$_f$ 0.30 (50% ethyl acetate in hexane)

INTERMEDIATE 20

4-Difluoromethoxy-2-ethylbenzooxazole-7-carboxylic acid 4-nitrophenyl ester para-Nitrophenol (0.95 g), 4-dimethylaminopyridine (80 mg) and 1-(3-dimethylaminopropyl)-3-ethylcarbodiimide hydrochloride (2.4 g) were added to a stirred suspension of 4-difluoromethoxy-2-ethylbenzooxazole-7-carboxylic acid (1.6 g) in dry dichloromethane (60 ml) under an atmosphere of nitrogen. The reaction mixture was stirred at room temperature for 18 hours. Water (20 ml) was added and the aqueous layer extracted with dichloromethane (400 ml). The organic layer was washed with water (80 ml), separated, dried over magnesium sulphate, filtered and the solvent removed in vacuo. Purification by column chromatography on silica eluting with 1:4 ethyl acetate/heptane to 1:1:2 ethyl acetate/dichloromethane/heptane afforded the title compound as a pale yellow solid (1.9 g)

TLC R$_f$ 0.39 (20% ethyl acetate in hexane).

The following compounds were prepared in a similar manner to the above:

INTERMEDIATE 21

2-Ethyl-4-methoxybenzooxazole-7-carboxylic acid 4-nitrophenyl ester

Starting from 2-ethyl-4-methoxybenzooxazole-7-carboxylic acid (0.57 g). Purification by column chromatography on silica eluting with 1:1 ethyl acetate-hexane afforded the title compound as a cream solid (0.64 g).

TLC R$_f$ 0.30 (50% ethyl acetate in hexane).

INTERMEDIATE 22

4-Difluoromethoxy-2-(morpholin-4-yl)-benzooxazole-7-carboxylic acid 4-nitrophenyl ester Starting from 4-difluoromethoxy-2-(morpholin-4-yl)-benzooxazole-7-carboxylic acid (0.69 g). Purification by column chromatography on silica eluting with 2.5% methanol in dichloromethane afforded the title compound as a white solid (0.49 g).

TLC R$_f$ 0.51 (10% methanol in dichloromethane).

INTERMEDIATE 23

4-Difluoromethoxy-2-ethylbenzooxazole-7-carboxylic acid 4-nitrophenyl ester

Starting from 4-difluoromethoxy-2-ethylbenzooxazole-7-carboxylic acid (0.256 g). Trituration with diethyl ether afforded the title compound as a pale yellow solid (0.18 g).

TLC R$_f$ 0.47 (50% ethyl acetate in heptane).

INTERMEDIATE 24

4-Difluoromethoxy-2-(piperidin-1-yl)-benzooxazole-7-carboxylic acid 4-nitrophenyl ester Starting from 4-difluoromethoxy-2-(piperidin-1-yl)-benzooxazole-7-carboxylic acid (0.5 g). Purification by column chromatography on silica eluting with 2.5% methanol in dichloromethane afforded the title compound as a white solid (0.35 g).

TLC R$_f$ 0.56 (10% methanol in dichloromethane).

INTERMEDIATE 25

2-(zetidin-1-yl)-4-difluoromethoxybenzooxazole-7-carboxylic acid 4-nitrophenyl ester Starting from 4-difluoromethoxy-2-(morpholin-4-yl)-benzooxazole-7-carboxylic acid (0.25 g). Purification by trituration with diethyl ether afforded the title compound as a pale yellow solid (0.182 g).

TLC R$_f$ 0.47 (50% ethyl acetate in heptane).

INTERMEDIATE 26

5-Ethyl-3-methylisoxazol-4-ylamine To a solution/suspension of 5-ethyl-3-methyl-4-nitroisoxazole (0.30 g) in water (10 ml) cooled to 0° C. was added ammonium chloride (2.5 g) followed by zinc powder (1.1 g) portionwise. The reaction mixture was allowed to warm to room temperature, stirred for 90 mins and extracted with ethyl acetate (2×50 ml). The organic layers were combined, dried over magnesium sulphate, filtered and the solvent removed in vacuo to afford the title compound as a yellow oil (0.173 g).

TLC R$_f$ 0.49 (ethyl acetate).

INTERMEDIATE 27

5-Methyl-3-trifluoromethylisoxazole-4-carboxylic acid

A solution of 5-methyl-3-trifluoromethylisoxazole-4-carboxylic acid ethyl ester (2.0 g) and sodium hydroxide (1.1 g) in tetrahydrofuran/water (20 ml/20 ml) was heated at reflux for 18 hours. The tetrahydrofuran was removed in vacuo and the aqueous residue washed with ethyl acetate (50 ml), acidified to pH2 with conc. hydrochloric acid and extracted with ethyl acetate (100 ml). The organic layer was washed with brine (50 ml), separated, dried over magnesium sulphate, filtered and concentrated in vacuo to afford the title compound as a peach-coloured solid (1.4 g).

TLC R$_f$ 0.60 (50% ethyl acetate in hexane).

INTERMEDIATE 28

(3-Ethyl-5-methylisoxazol-4-yl)-carbamic acid 2-trimethylsilanylethyl ester

A solution of 3-ethyl-5-methyl-isoxazole-4-carboxylic acid (1.0 g), diphenylphosphoryl azide (1.4 ml) and triethylamine (0.9 ml) in toluene (20 ml) under an atmosphere of nitrogen was heated at 80° C. for 2 hours. 2-(Trimethylsilyl)-ethanol was added dropwise and heating at 80° C. continued for 18 hours. The solvent was removed in vacuo and the residue dissolved in ethyl acetate (100 ml), washed with 1N sodium hydroxide solution (2×25 ml) and washed with brine (25 ml). The organic layer was separated, dried over magnesium sulphate, filtered and the solvent removed in vacuo. Purification by column chromatograhy on silica eluting with 20% ethyl acetate in hexane afforded the title compound as a colourless oil (1.2 g).

TLC R$_f$ 0.39 (50% ethyl acetate in hexane).

The following compound was prepared in a similar manner to the above.

INTERMEDIATE 29

(5-Methyl-3-trifluoromethylisoxazol-4-yl)-carbamic acid 2-trimethylsilanylethyl ester Starting from 5-methyl-3-trifluoromethylisoxazole-4-carboxylic acid (0.9 g). Purification by column chromatogaphy on silica eluting with 20% ethyl acetate in hexane afforded the title compound as a pale yellow oil (0.59 g).

TLC R$_f$ 0.45 (20% ethyl acetate in hexane).

INTERMEDIATE 30

3-Ethyl-5-methylisoxazol-4-ylamine

A solution of (3-ethyl-5-methylisoxazol-4-yl)-carbamic acid 2-trimethylsilanylethyl ester (1.8 g) in tetrabutylammonium fluoride (26.7 ml of a 1.0M solution in tetrahydrofuran) was heated at 50° C. for 30 mins. The solvent was removed in vacuo and the residue dissolved in ethyl acetate (150 ml), washed with sodium hydrogencarbonate solution (30 ml), washed with water (30 ml) and washed with brine (30 ml). The organic layer was separated, dried over magnesium sulphate, filtered and the solvent removed in vacuo. Purification by column chromatography on silica eluting with 50–100% ethyl acetate in hexane afforded the title compound as a yellow oil (0.35 g).

TLC $R_f$ 0.16 (50% ethyl acetate in hexane).

The folowing compound was prepared in similar manner to the above.

INTERMEDIATE 31
5-Methyl-3-trifluoromethylisoxazol-4-ylamine

Starting from (5-methyl-3-trifluoromethylisoxazol-4-yl)-carbamic acid 2-trimethylsilanylethyl ester (0.59 g). Purification by column chromatography on silica eluting with 20% ethyl acetate in hexane afforded the title compound as a yellow liquid (0.18 g).

TLC $R_f$ 0.50 (50% ethyl acetate in hexane).

INTERMEDIATE 32
4-Chloro-2-methyl-2H-pyrazol-3-ylamine

To a solution of 2-methyl-2H-pyrazol-3-ylamine (0.30 g) in conc. hydrochloric acid (4 ml) heated to 85° C. was added dropwise hydrogen peroxide (0.67 ml of a 30% solution in water). Heating continued for 60 mins. After cooling to 0° C. the solution was taken to pH 11 using 46/48 w/w sodium hydroxides solution. The solid formed was filtered off and the filtrate extracted with ethyl acetate (4×5 ml). The combined organic layers were dried over magnesium sulphate, filtered and concentrated in vacuo. The resulting product was combined with the previously collected product to afford the title compound as a brown solid (0.13 g).

TLC $R_f$ 0.50 (10% methanol in dichloromethane).

INTERMEDIATE 33
4-Ethyl-2-methyl-2H-pyrazol-3-ylamine

To a suspension of sodium (2.0 g) in dry tetrahydrofuran (100 ml) under an atmosphere of nitrogen was added n-butyraldehyde (3.0 g) and ethyl formate (3.3 g) dropwise. The mixture was stirred at room temperature for 3 days. After cooling to −10° C. the mixture was neutralised by addition of acetic acid and the resulting solid removed by filtration. The filtrate was concentrated in vacuo and the residue dissolved in ethanol (50 ml) and treated with methyl hydrazine (2.0 g) and glacial acetic acid (13.8 g) and heated at reflux for 2 hours. The solvent was removed in vacuo and the residue dissolved in ethyl acetate (100 ml) and extracted with 2M hydrochloric acid (2×100 ml). The aqueous layers were combined, basified with 6N sodium hydroxide and extracted with ethyl acetate (2×100 ml). The organic extracts were combined, dried over magnesium sulphate, filtered and the solvent removed in vacuo. Purification by column chromatography on silica eluting with 5% methanol in dichloromethane affoeded the title compound as a tan oil (1.8 g).

TLC $R_f$ 0.33 (10% methanol in dichloromethane).

INTERMEDIATE 34
5-Amino-1-ethyl-1H-imidazole-4-carbonitrile

To a solution/suspension of 5-amino-1H-imidazole-4-carbonitrile (2.16 g) in tetrahydrofuran/N,N-dimethylformamide under an atmosphere of nitrogen was added potassium carbonate (3.3 g) and iodoethane (1.9 mL). The reaction mixture was stirred at room temperature for 60 hours, filtered and the solvent removed in vacuo. Purification by column chromatography on silica eluting with 2–5% methanol in dichloromethane afforded the title compound as an off-white solid (0.60 g).

TLC $R_f$ 0.42 (5% methanol in dichloromethane).

EXAMPLE 1
4-Difluoromethoxy-2-ethylbenzooxazole-7-carboxylic acid (3,5-dimethylisoxazole-4-yl)-amide Oxalyl chloride (0.2 ml) was added to a suspension of 4-difluoromethoxy-2-(piperidin-1-yl)-benzooxazole-7-carboxylic acid (0.3 g) in dichloromethane (20 ml) at room temperature under an atmosphere of nitrogen. Three drops of N,N-dimethylformamide were added, and the mixture stirred for 18 hours. The solvent was removed in vacuo and the residue dissolved in dichloromethane (20 ml). The resulting solution was added to a mixture of 3,5-dimethylisoxazol-4-ylamine (0.16 g) and triethylamine (0.2 ml) in dichloromethane (20 ml) at room temperature under an atmosphere of nitrogen. The mixture was stirred for 2 hours, then washed with aqueous sodium bicarbonate (2×20 ml) and water (20 ml). The organics were dried over magnesium sulphate, filtered and the solvent removed in vacuo. Purification by column chromatography on silica eluting with 50% ethyl acetate in heptane afforded the title compound as a white solid (0.29 g).

TLC $R_f$ 0.65 (ethyl acetate).

Mass spectrum m/z 350 (M−1)

The following compounds were prepared in a similar manner to the above.

EXAMPLE 2
4-Difluoromethoxy-2-ethylbenzooxazole-7-carboxylic acid (3-methylisoxazole-4-yl)-amide Starting from 4-difluoromethoxy-2-ethylbenzooxazole-7-carboxylic acid (150 mg) and 5-methylisoxazol-4-ylamine (60 mg). Purification by column chromatography on silica eluting with 50% ethyl acetate in heptane afforded the title compound as a white solid (110 mg).

TLC $R_f$ 0.32 (ethyl acetate).

M.p. 103–104.5° C.

EXAMPLE 3
4-Difluoromethoxy-2-ethylbenzooxazole-7-carboxylic acid (5-ethyl-3-methylisoxazole-4-yl)-amide Starting from 4-difluoromethoxy-2-ethylbenzooxazole-7-carboxylic acid (92 mg) and 5-ethylisoxazol-4-ylamine (60 g). Purification by column chromatography on silica eluting 30%–50% ethyl acetate in heptane afforded the title compound as a white solid (39 mg).

TLC $R_f$ 0.49 (50% ethyl acetate in heptane).

M.p. 120–122° C.

EXAMPLE 4
4-Difluoromethoxy-2-ethylbenzooxazole-7-carboxylic acid (3-ethyl-5-methylisoxazole-4-yl)-amide Starting from 4-difluoromethoxy-2-ethylbenzooxazole-7-carboxylic acid (0.20 g) and 3-ethyl-5-methylisoxazol-4-ylamine (0.20 g). Purification by column chromatography on silica eluting 20–50% ethyl acetate in heptane afforded, after trituration with diethyl ether-hexane, the title compound as a white solid (0.155 g).

TLC $R_f$ 0.50 (50% ethyl acetate in heptane).

M.p. 123–124° C.

EXAMPLE 5
4-Difluoromethoxy-2-ethylbenzooxazole-7-carboxylic acid (2-ethyl-4-methyl-2H-pyrazol-3-yl)-amide Starting from 4-difluoromethoxy-2-ethylbenzooxazole-7-carboxylic acid (150 mg) and 2-ethyl-4-methyl-2H-pyrazol-3-ylamine (90 mg). Purification by column chromatography on silica eluting 2:1 ethyl acetate-heptane followed by ethyl acetate afforded the title compound as a white solid (85 mg).

TLC $R_f$ 0.68 (ethyl acetate).

M.p. 122–124° C.

EXAMPLE 6
4-Methoxy-2-ethylbenzooxazole-7-carboxylic acid (3,5-dimethylisoxazol-4-yl)-amide Starting from 4-methoxy-2-ethylbenzooxazole-7-carboxylic acid (0.23 g) and 3,5-dimethylisoxazol-4-ylamine (0.1 g). Purification by column chromatography on silica eluting with ethyl acetate afforded the title compound as a cream solid (0.18 g).

TLC $R_f$ 0.48 (ethyl acetate).
M.p. 157–158.5° C.

EXAMPLE 7
4-Difluoromethoxy-2-ethylbenzooxazole-7-carboxylic acid (2-methyl-2H-pyrazol-3-yl)-amide Starting from 4-difluoromethoxy-2-ethylbenzooxazole-7-carboxylic acid (0.23 g) and 2-methyl-2H-pyrazol-3-ylamine (0.1 g). Purification by column chromatography on silica eluting with 5% methanol in dichloromethane afforded the title compound as a cream solid (0.10 g).

TLC $R_f$ 0.54 (10% methanol in dichloromethane).
M.p. 111–112.5° C.

EXAMPLE 8
4-Difluoromethoxy-2-(morpholin-4-yl)-benzooxazole-7-carboxylic acid (3,5-dimethylisoxazo-4-yl)-amide Starting from 4-difluoromethoxy-2-(morpholin-4-yl)-benzooxazole-7-carboxylic acid (0.20 g) and 3,5-dimethylisoxazo-4-ylamine (0.08 g). Purification by column chromatography on silica eluting with 50–100% ethyl acetate in heptane afforded the title compound as a white solid (0.18 g).

TLC $R_f$ 0.67 (ethyl acetate).
Mass spectrum m/z 409' (M+1)

EXAMPLE 9
4Methoxy-2-(morpholin-4-yl)-benzooxazole-7-carboxylic acid (3,5-dimethylisoxazo-4-yl)-amide Starting from 4-difluoromethoxy-2-(morpholin4-yl)-benzooxazole-7-carboxylic acid (0.30 g) and 3,5-dimethylisoxazo-4-ylamine (0.145 g). Purification by column chromatography on silica eluting with 0–10% methanol in ethyl acetate afforded the title compound as a white solid (0.12 g).

TLC $R_f$ 0.24 (ethyl acetate).
Mass spectrum m/z 373' (M+1)

EXAMPLE 10
2-(Azetidin-1-yl)-4-difluoromethoxy-benzooxazole7-carboxylic acid (3,5-dimethyl-isoxazol-4-yl)-amide Starting from 2-(azetidin-1-yl)-4-difluoromethoxy-benzooxazole-7-carboxylic acid (210 mg) and 3,5-dimethylisoxazo-4-ylamine (176 mg). Purification by column chromatography on silica eluting with 50% ethyl acetate in heptane followed by preparative HPLC afforded the title compound as a pale orange solid (31 mg).

TLC $R_f$ 0.31 (70% ethyl acetate in heptane).
M.p. 181–182° C.

EXAMPLE 11
4-Difluoromethoxy-2-ethylbenzooxazole-7-carboxylic acid (2-ethyl-2H-pyrazol-3-yl)-amide Hydrazine hydrate (0.94 ml) was added dropwise to acrylonitrile (2.0 ml) cooled in an ice bath under an atmosphere of nitrogen. The mixture was heated to 50° C. for 45 minutes. After cooling to room temperature it was diluted with ethanol (5.0 ml). Acetaldehyde (1.68 ml) was added, and the mixture heated to reflux for 1 hour. The ethanol was removed in vacuo and added to a solution of sodium (0.7 g) predissolved in t-butanol (25 ml) at 45° C. under an atmosphere of nitrogen. The mixture was heated to reflux for 18 hours. It was then poured into water (100 ml) and extracted with ethyl acetate (3×100 ml). The combined organics were dried over magnesium sulphate, filtered and the solvent removed in vacuo to give crude 2-ethyl-2H-pyrazole-3-ylamine as an orange gum. This was dissolved in dichloromethane (5 ml) containing triethylamine (0.09 ml) at room temperature under an atmosphere of nitrogen. A solution of 4-difluoromethoxy-2-ethylbenzooxazole-7-carbonyl chloride [previously prepared from 4-difluoromethoxy-2-ethylbonzooxazole-7-carboxylic acid (0.15 g)] in dichloromethane (5 ml) was added, and the mixture stirred for 2 hours. The solvent was removed in vacuo and purified by column chromatography on silica eluting with 2:1 heptane-ethyl acetate followed by ethyl acetate and then recrystallised from ethyl acetate-hexane to give the title compound as a pale yellow solid (21 mg).

TLC $R_f$ 0.59 (ethyl acetate).
M.p. 94–96° C.

EXAMPLE 12
4-Difluoromethoxy-2-ethylbenzooxazole-7-carboxylic acid (4-cyano-2-methyl-2H-pyrazol-3-yl)-amide Sodium bis(trimethylsilyl)amide (0.53 ml) was added to a solution of 5-amino-1-methyl-1H-pyrazole-4-carbonitrile (65 mg) in N,N-dimethylformamide (5 ml) at room temperature under an atmosphere of nitrogen. The mixture was stirred for 10 minutes before addition of 4-difluoromethoxy-2-ethylbenzooxazole-7-carboxylic acid 4-nitrophenyl ester (100 mg), then for 90 minutes. It was quenched with water (1 ml) and the solvent removed in vacuo. Purification by column chromatography on silica eluting with 2:1 heptane-ethyl acetate afforded the title compound as a white solid (25 mg).

TLC $R_f$ 0.64 (ethyl acetate).
M.p. 150–152° C.

The following compounds were prepared in a similar manner to the above.

EXAMPLE 13
4-Difluoromethoxy-2-ethylbenzooxazole-7-carboxylic acid (4-bromo-2-methyl-2H-pyrazol-3-yl)-amide Starting from 4-difluoromethoxy-2-ethylbenzooxazole-7-carboxylic acid 4-nitro-phenyl ester (100 mg) and 4-bromo-2-methyl-2H-pyrazol-3-ylamine (93 mg). Purification by column chromatography on silica eluting with 1–5% methanol in dichloromethane afforded, after trituration with diethyl ether, the title compound as a white solid (7 mg).

TLC $R_f$ 0.57 (10% methanol in dichloromethane).
M.p. 189–191° C.

EXAMPLE 14
4-Difluoromethoxy-2-ethylbenzooxazole-7-carboxylic acid (2-methyl-2H-pyrazole-3-yl)-amide Starting from 4-difluoromethoxy-2-ethylbenzooxazole-7-carboxylic acid 4-nitro-phenyl ester (100 mg) and 2-methyl-2H-pyrazole-3-ylamine (51 mg). Purification by column chromatography on silica eluting with ethyl acetate afforded, after trituration with a mixture of diethyl ether and hexane, the title compound as a pale yellow solid (14mg).

TLC $R_f$ 0.31 (ethyl acetate).
M.p. 123–124° C.

EXAMPLE 15
4-Difluoromethoxy-2-ethylbenzooxazole-7-carboxylic acid (5-cyano-3-methyl-3H-imidazol-4-yl)-amide Starting from 4-difluoromethoxy-2-ethylbenzooxazole-7-carboxylic acid 4-nitro-phenyl ester (100 mg) and 5-amino- 1-methyl-1H-imidazole-4-carbonitrile (65 mg). Purification by column chromatography on silica eluting with 0–5% methanol in ethyl acetate afforded, after trituration with diethyl ether, the title compound as a white solid (33 mg)
TLC $R_f$ 0.59 (10% methanol in ethyl acetate).
M.p. 166–167° C.

EXAMPLE 16
4-Difluoromethoxy-2-ethylbenzooxazole-7-carboxylic acid (4-cyano-3-ethyl-3H-imidazole-4-yl)-amide Starting from 4-difluoromethoxy-2-ethylbenzooxazole-7-carboxylic acid 4-nitrophenyl ester (100 mg) and 5-amino-1-ethyl-1H-imidazole-4-carbonitrile (110 mg). Purification by column chromatography on silica eluting with ethyl acetate afforded, after trituration with 2.5% methanol in dichloromethane, the title compound as a white solid (70 mg).
TLC $R_f$ 0.33 (2.5% methanol in ethyl acetate).
M.p. 163–164° C.

EXAMPLE 17
4-Difluoromethoxy-2-(morpholin-4-yl)-benzooxazole-7-carboxylic acid (4-cyano-2-methyl-2H-pyrazol-3-yl)-amide Starting from 4-difluoromethoxy-2-(morpholin-4-yl)-benzooxazole-7-carboxylic acid 4-nitrophenyl ester (100 mg) and 5-amino-1-methyl-1H-pyrazole-4-carbonitrile (56 mg). Purification by column chromatography on silica eluting with 5% methanol in dichloromethane followed by preparative thin layer chromatography eluting with 3% methanol in dichloromethane afforded the title compound as a white solid (28 mg).
TLC $R_f$ 0.22 (3% methanol in dichloromethane).
Mass spectrum m/z 417 (M−1)

EXAMPLE 18
4-Methoxy-2-(morpholin-4-yl)-benzooxazole-7-carboxylic acid (4-cyano-2-methyl-2H-pyrazol-3-yl)-amide Starting from 4-methoxy-2-(morpholin-4-yl)-benzooxazole-7-carboxylic acid 4-nitro-phenyl ester (200 mg) and 5-amino-1-methyl-1H-pyrazole-4-carbonitrile (122 mg). Purification by column chromatography on silica eluting with 80% ethyl acetate in heptane followed by 1% methanol in dichloromethane afforded, after trituration with diethyl ether, the title compound as a white solid (132 mg).
TLC $R_f$ 0.46 (10% methanol in dichloromethane).
M.p. 306–308° C.

EXAMPLE 19
4-Difluoromethoxy-2-(piperidin-1-yl)-benzooxazole-7-carboxylic acid (4-cyano-2-methyl-2H-pyrazol-3-yl)-amide Starting from 4-difluoromethoxy-2-(piperidin-1-yl)-benzooxazole-7-carboxylic acid 4-nitro-phenyl ester (0.35 g) and 5-amino-1-methyl-1H-pyrazole-4-carbonitrile (0.197 g). Purification by column chromatography on silica eluting with 50% ethyl acetate in heptane afforded the title compound as a white solid (50 mg).
TLC $R_f$ 0.71 (ethyl acetate).
M.p. 234–236° C.

EXAMPLE 20
2-(Azetidin-1-yl)-4-difluoromethoxybenzooxazole-7-carboxylic acid (4-cyano-2-methyl-2H-pyrazol-3-yl)-amide Starting from 2-(azetidin-1-yl)-4-difluoromethoxybenzooxazole-7-carboxylic acid 4-nitrophenyl ester (178 mg) and 5-amino-1-methyl-1H-pyrazole-4-carbonitrile (107 mg). Purification by column chromatography on silica eluting with 3% methanol in dichloromethane followed by trituration in diethyl ether afforded the title compound as a white solid (124 mg).
TLC $R_f$ 0.31 (ethyl acetate).
M.p. 247–248° C.

EXAMPLE 21
4-Difluoromethoxy-2-ethylbenzooxazole-7-carboxylic acid (2,4-dimethyl-2H-pyrazo-3-yl)-amide Sodium hydride (45 mg of a 60% dispersion in oil) was added to a solution of 2,4-dimethyl-2H-pyrazo-3-ylamine (124 mg) in N,N-dimethylformamide (10 ml) at room temperature under an atmosphere of nitrogen. The mixture was stirred for 5 minutes before addition of 4-difluoromethoxy-2-ethylbenzooxazole-7-carboxylic acid 4-nitro-phenyl ester (200 mg), then for 75 minutes. It was quenched with water (0.2 ml) and the solvent removed in vacuo. Purification by column chromatography on silica eluting with 50–100% ethyl acetate in heptane afforded the title compound as an off white solid (75 mg).
TLC $R_f$ 0.30 (ethyl acetate).
Mass spectrum m/z 351 (M+1)

The following compounds were prepared in a similar manner to the above.

EXAMPLE 22
4-Difluoromethoxy-2-ethylbenzooxazole-7-carboxylic acid (4-chloro-2-methyl-2H-pyrazo-3-yl)-amide Starting from 4-difluoromethoxy-2-ethylbenzooxazole-7-carboxylic acid 4-nitrophenyl ester (100 mg) and 4-chloro-2-methyl-2H-pyrazo-3-ylamine (69 mg). Purification by column chromatography on silica eluting with 60% ethyl acetate in heptane afforded, after trituration with diethyl ether, the title compound as a pale yellow solid (36 mg).
TLC $R_f$ 0.23 (10% ethyl acetate in dichloromethane).
Mass spectrum m/z 371 (M+1)

EXAMPLE 23
4-Difluoromethoxy-2-ethylbenzooxazole-7-carboxylic acid (4-ethyl-2-methyl-2H-pyrazol-3-yl)-amide Starting from 4-difluoromethoxy-2-ethylbenzooxazole-7-carboxylic acid 4-nitro-phenyl ester (100 mg) and 4-ethyl-2-methyl-2H-pyrazol-3-ylamine (64 mg). Purification by column chromatography on silica eluting with 5% methanol in dichloromethane afforded the title compound as an off white solid (55 mg).
TLC $R_f$ 0.12 (50% ethyl acetate in hexane).
Mass spectrum m/z 365 (M+1)

EXAMPLE 24
2-Ethyl-4-methoxybenzooxazole-7-carboxylic acid (4-chloro-2-methyl-2H-pyrazol-3-yl)-amide Starting from 4-difluoromethoxy-2-ethylbenzooxazole-7-carboxylic acid 4-nitro-phenyl ester (100 mg) and 4-chloro-2-methyl-2H-pyrazol-3-yl)-amide (77 mg) Purification by column chromatography on silica eluting with ethyl acetate afforded, after trituration with diethyl ether, the title compound as a pale pink solid (44 mg).
TLC $R_f$ 0.42 (ethyl acetate).
M.p. 220–221.5° C.

EXAMPLE 25
4-Difluoromethoxy-2-ethylbenzooxazole-7-carboxylic acid (3-methylisoxazol-4-yl)-amide Cyanuric chloride (24 mg) was added to a suspension of 4-difluoromethoxy-2-ethylbenzooxazole-7-carboxylic acid (0.1 g) in dichloromethane (20 ml) at room temperature under an atmosphere of nitrogen. Triethylamine (0.07 ml) was added dropwise, followed by 3-methylisoxazol-4-ylamine (46 mg) in dichloromethane (5 ml). The reaction was left to stir for 2 hours before evaporation of the solvent in vacuo. Purification by column chromatography on silica eluting with 50% ethyl acetate in heptane afforded, after trituration with diethyl ether-hexane, the title compound as a white solid (5 mg).

TLC $R_f$ 0.29 (50% ethyl acetate in heptane).
M.p. 157–158° C.

The following compound was prepared in a similar manner to the above.

EXAMPLE 26

4-Difluoromethoxy-2-ethylbenzooxazole-7-carboxylic acid (5-methyl-3-trifluoromethylisoxazol-4-yl)-amide Starting from 4-difluoromethoxy-2-ethylbenzooxazole-7-carboxylic acid (0.1 g) and 5-methyl-3-trifluoromethylisoxazol-4-ylamine (78 mg). Purification by column chromatography eluting with 20–30% ethyl acetate in hexane afforded the title compound as a white solid (16 mg).

TLC $R_f$ 0.24 (30% ethyl acetate in hexane).
M.p. 131–133° C.

What is claimed is:

1. A compound of the formula

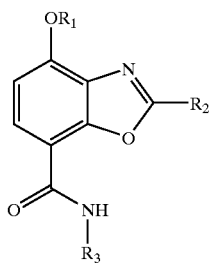

(i)

wherein
$R_1$ is $C_{1-3}$ alkyl optionally substituted with one or more fluorines;
$R_2$ is $C_{1-6}$ alkyl, cycloalkyl or $NR_4R_5$;
$R_3$ is a pyrazole, imidazole or isoxazole group of partial formula (A), (B) or (C)

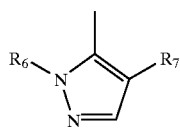

(A)

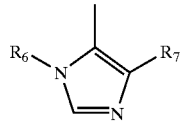

(B)

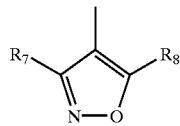

(C)

$NR_4R_5$ is a nitrogen-containing heterocyclic ring;
$R_6$ is $C_{1-3}$ alkyl; and
$R_7$ and $R_8$, which are the same or different, each represents $C_{1-3}$ alkyl, halogen, $CF_3$ or CN;
or a pharmaceutically-acceptable salt thereof.

2. The compound of claim 1, wherein $R_1$ is $CH_3$ or $CHF_2$.
3. The compound of claim 1, wherein $R_3$ is a pyrazole or isoxazole group.

4. The compound of claim 3, wherein $R_3$ is a pyrazole group, $R_6$ is $CH_3$ and $R_7$ is CN, $CH_3$ or $CF_3$.
5. The compound of claim 3, wherein $R_3$ is an isoxazole group, $R_7$ is $CH_3$, $CF_3$ or CN and $R_8$ is $CH_3$, $CF_3$ or CN.
6. The compound of claim 1, the group consisting of 4-difluoromethoxy-2-ethylbenzooxazole-7-carboxylic acid (3,5-dimethylisoxazole-4-yl)-amide,
4-difluoromethoxy-2-ethylbenzooxazole-7-carboxylic acid (3-methylisoxazole-4-yl)-amide,
4-difluoromethoxy-2-ethylbenzooxazole-7-carboxylic acid (5-ethyl-3-methylisoxazole-4-yl)-amide,
4-difluoromethoxy-2-ethylbenzooxazole-7-carboxylic acid (3-ethyl-5-methylisoxazole-4-yl)-amide,
4-difluoromethoxy-2-ethylbenzooxazole-7-carboxylic acid (2-ethyl-4-methyl-2H-pyrazol-3-yl)-amide,
4-methoxy-2-ethylbenzooxazole-7-carboxylic acid (3,5-dimethylisoxazol-4-yl)-amide,
4-difluoromethoxy-2-ethylbenzooxazole-7-carboxylic acid (2-methyl-2H-pyrazol-3-yl)-amide,
4-difluoromethoxy-2-(morpholin-4-yl)-benzooxazole-7-carboxylic acid (3,5-dimethylisoxazo-4-yl)-amide,
4-methoxy-2-(morpholin-4-yl)-benzooxazole-7-carboxylic acid (3,5-dimethylisoxazo-4-yl)-amide,
2-(azetidin-1-yl)-4-difluoromethoxy-benzooxazole-7-carboxylic acid (3,5-dimethyl-isoxazol-4-yl)-amide,
4-difluoromethoxy-2-ethylbenzooxazole-7-carboxylic acid (2-ethyl-2H-pyrazol-3-yl)-amide,
4-difluoromethoxy-2-ethylbenzooxazole-7-carboxylic acid (4-cyano-2-methyl-2H-pyrazol-3-yl)-amide,
4-difluoromethoxy-2-ethylbenzooxazole-7-carboxylic acid (4-bromo-2-methyl-2H-pyrazol-3-yl)-amide,
4-difluoromethoxy-2-ethylbenzooxazole-7-carboxylic acid (2-methyl-2H-pyrazole-3-yl)-amide,
4-difluoromethoxy-2-ethylbenzooxazole-7-carboxylic acid (5-cyano-3-methyl-3H-imidazol-4-yl)-amide
4-difluoromethoxy-2-ethylbenzooxazole-7-carboxylic acid (4-cyano-3-ethyl-3H-imidazole-4-yl)-amide,
4-difluoromethoxy-2-(morpholin-4-yl)benzooxazole-7-carboxylic acid (4-cyano-2-methyl-2H-pyrazol-3-yl)-amide,
4-methoxy-2-(morpholin-4-yl)-benzooxazole-7-carboxylic acid (4-cyano-2-methyl-2H-pyrazol-3-yl)-amide,
4-difluoromethoxy-2-(piperidin-1-yl)-benzooxazole-7-carboxylic acid (4-cyano-2-methyl-2H-pyrazol-3-yl)-amide,
2-(azetidin-1-yl)-4-difluoromethoxybenzooxazole-7-carboxylic acid (4-cyano-2-methyl-2H-pyrazol-3-yl)-amide,
4-difluoromethoxy-2-ethylbenzooxazole-7-carboxylic acid (2,4-dimethyl-2H-pyrazo-3-yl)-amide,
4-difluoromethoxy-2-ethylbenzooxazole-7-carboxylic acid (4-chloro-2-methyl-2H-pyrazo-3-yl)-amide,
4-difluoromethoxy-2-ethylbenzooxazole-7-carboxylic acid (4-ethyl-2-methyl-2H-pyrazol-3-yl)-amide,
2-ethyl-4-methoxybenzooxazole-7-carboxylic acid (4-chloro-2-methyl-2H-pyrazol-3-yl)-amide,
4-difluoromethoxy-2-ethylbenzooxazole-7-carboxylic acid (3-methylisoxazole-4-yl)-amide, and
4-difluoromethoxy-2-ethylbenzooxazole-7-carboxylic acid (5-methyl-3-trifluoromethylisoxazol-4-yl)-amide.

7. A composition for use in therapy, comprising a compound of claim 1 and a pharmaceutically acceptable carrier or diluent.

8. A method for the treatment of a disease state in a person or animal, wherein the disease state is an inflammatory disease or autoimmune disease, said method comprising administering to a person or animal an effective amount of the compound of claim 1.

9. A method for the treatment of a disease state in a person or animal, wherein the disease state is selected from the group consisting of asthma, chronic bronchitis, chronic pulmonary inflammatory disease, chronic obstructive airways disease, atopic dermatitis, allergic rhinitis, psoriasis, arthritis, rheumatoid arthritis, joint inflammation, ulcerative colitis, Crohn's disease, atopic eczema, stroke, bone resorption disease, multiple sclerosis and inflammatory bowel disease, said method comprising administering to a person or animal an effective amount of the compound of claim 1.

10. A method for the treatment of a disease state in a person or animal, wherein the disease state is selected from the group consisting of urticaria, allergic conjunctivitis, vernal conjunctivitis, inflammation of the eye, allergic responses in the eye, eosinophilic granuloma, gouty arthritis and other arthritic conditions, adult respiratory distress syndrome, diabetes insipidus, keratosis, cerebral senility, multi-infarct dementia, senile dementia, memory impairment associated with Parkinson's disease, depression, cardiac arrest, intermittent claudication, rheumatoid spondylitis, osteoarthritis, sepsis, septic shock, endotoxic shock, gram negative sepsis, toxic shock syndrome, acute respiratory distress syndrome, cerebral malaria, silicosis, pulmonary sarcoidosis, reperfusion injury, graft vs host reaction, allograft rejection, infection-related fever or myalgia, malaria, ARC, cachexia, keloid formation, scar tissue formation, pyresis, systemic lupus erythematosus, type 1 diabetes mellitus, Bechet's disease, anaphylactoid purpura nephritis, chronic glomerulonephritis, tarditive dyskinesia, yeast or fungal infection, conditions requiring gastroprotection, and neurogenic inflammatory disease associated with irritation and pain, said method comprising administering to a person or animal an effective amount of the compound of claim 1.

11. A method of the treatment of a disease state in a person or animal, wherein the disease state is asthma, said method comprising administering to a person or animal an effective amount of the compound of claim 1.

12. A method for the treatment of a disease state in a person or animal, wherein the disease state is chronic obstructive airway disease or chronic bronchitis, said method comprising administering to a person or animal an effective amount of the compound of claim 1.

13. The compound of claim 2, wherein $R_3$ is a pyrazole or isoxazole group.

14. The compound of claim 13, wherein $R_3$ is a pyrazole group, $R_6$ is $CH_3$ and $R_7$ is CN, $CH_3$, or $CF_3$.

15. The compound of claim 13, wherein $R_3$ is an isoxazole group, $R_7$ is $CH_3$, $CF_3$ or CN and $R_8$ is $CH_3$, $CF_3$ or CN.

* * * * *

UNITED STATES PATENT AND TRADEMARK OFFICE
CERTIFICATE OF CORRECTION

PATENT NO.    : 6,403,791 B1
DATED         : June 11, 2002
INVENTOR(S)   : Hazel Joan Dyke, Alan Findlay Haughan, Christopher Lowe, George Martin Buckley, Richard John Davenport, Andrew Sharpe, Hannah Jayne Kendall, Verity Margaret Sabin, John Gary Montana and Catherine Louise Picken It is certified that error appears in the above-identified patent and that said Letters Patent is hereby corrected as shown below:

Column 20,
Line 5, "the group consisting of" should read -- selected from the group consisting of --.

Column 22,
Line 17, "airway" should read -- airways --.

Signed and Sealed this

Eighth Day of October, 2002

Attest:

JAMES E. ROGAN
Attesting Officer        Director of the United States Patent and Trademark Office